United States Patent
Ikeda et al.

(10) Patent No.: US 10,167,861 B2
(45) Date of Patent: Jan. 1, 2019

(54) INFUSION PUMP

(71) Applicants: Namiki Precision Singapore Pte, Ltd., Singapore (SG); Adamant Namiki Precision Jewel Co., Ltd., Tokyo (JP)

(72) Inventors: Hisashi Ikeda, Tokyo (JP); Masahiro Koyama, Singapore (SG); Katsuya Kataoka, Tokyo (JP); Jun Araaki, Tokyo (JP)

(73) Assignees: Namiki Precision Singapore Pte. Ltd., Singapore (SG); Adamant Namiki Precision Jewel Co., Ltd., Tokyo (JP)

( * ) Notice: Subject to any disclaimer, the term of this patent is extended or adjusted under 35 U.S.C. 154(b) by 429 days.

(21) Appl. No.: 15/165,793

(22) Filed: May 26, 2016

(65) Prior Publication Data
US 2017/0342973 A1    Nov. 30, 2017

(51) Int. Cl.
*F04B 43/00* (2006.01)
*F04B 43/08* (2006.01)
(Continued)

(52) U.S. Cl.
CPC ......... *F04B 43/08* (2013.01); *A61M 5/16813* (2013.01); *F04B 7/0057* (2013.01); *F04B 43/009* (2013.01); *F04B 43/0072* (2013.01); *F04B 53/16* (2013.01); *F04B 53/22* (2013.01); *F04B 53/102* (2013.01)

(58) Field of Classification Search
CPC .... F04B 43/009; F04B 43/0081; F04B 43/08; F04B 43/0009; F04B 43/12; A61M 2005/1401; A61M 2005/1406; A61M 2005/1418; A61M 5/142; A61M 5/16813
See application file for complete search history.

(56) References Cited

U.S. PATENT DOCUMENTS 5,017,192 A * 5/1991 Dodge ................ A61M 39/287
                                                               251/7
5,219,327 A * 6/1993 Okada ............... A61M 5/14228
                                                          128/DIG. 12
(Continued)

FOREIGN PATENT DOCUMENTS

| JP | 2007023803 A | 2/2007 |
| JP | 2016059535 A | 4/2016 |
| WO | 2014123178 A1 | 8/2014 |

*Primary Examiner* — Charles Freay
*Assistant Examiner* — Thomas Fink
(74) *Attorney, Agent, or Firm* — Studebaker & Brackett PC

(57) ABSTRACT

The present invention is provided to suppress occurrence of free flow. An infusion pump includes: a sliding clamp closing and releasing an infusion tube; a pump body including a tube attachment portion to which the infusion tube is to be attached detachably and forcibly transferring liquid in the infusion tube; and a door pivotably supported by the pump body so that the tube attachment portion is openable and closable by the door. The pump body includes: a clamp attachment portion into which the sliding clamp having the infusion tube set therein is to be inserted and set; and a release operator being operated in the clamp attachment portion to transfer the sliding clamp from a close mode to a release mode, the release operator being configured to be locked, in response to opening movement of the door, so that the release operator is inoperable for releasing, and to be unlocked in response to closing movement of the door.

6 Claims, 18 Drawing Sheets

(51) Int. Cl.
*A61M 5/168* (2006.01)
*F04B 53/16* (2006.01)
*F04B 7/00* (2006.01)
*F04B 53/22* (2006.01)
*F04B 53/10* (2006.01)

(56) References Cited

U.S. PATENT DOCUMENTS

| | | | | |
|---|---|---|---|---|
| 5,290,158 A * | 3/1994 | Okada | | A61M 5/142 |
| | | | | 417/474 |
| 5,290,239 A * | 3/1994 | Classey | | A61M 39/287 |
| | | | | 128/DIG. 12 |
| 5,401,256 A * | 3/1995 | Stone | | A61M 39/287 |
| | | | | 251/10 |
| 5,437,635 A * | 8/1995 | Fields | | A61M 5/16813 |
| | | | | 604/65 |
| 6,117,115 A * | 9/2000 | Hill | | A61M 5/16813 |
| | | | | 604/250 |
| 6,692,241 B2 * | 2/2004 | Watanabe | | A61M 5/14228 |
| | | | | 417/477.2 |
| 9,272,129 B2 * | 3/2016 | Howlett | | A61M 39/286 |
| 9,677,555 B2 * | 6/2017 | Kamen | | G06F 19/3418 |
| 2006/0011873 A1 * | 1/2006 | Clarke | | F16K 7/066 |
| | | | | 251/4 |
| 2010/0040481 A1 * | 2/2010 | Wolff | | A61M 5/14216 |
| | | | | 417/53 |
| 2010/0268161 A1 * | 10/2010 | Traversaz | | A61M 5/14244 |
| | | | | 604/151 |
| 2012/0035581 A1 * | 2/2012 | Travis | | A61M 39/28 |
| | | | | 604/500 |
| 2012/0238991 A1 * | 9/2012 | Zhang | | A61M 5/168 |
| | | | | 604/500 |
| 2013/0138074 A1 * | 5/2013 | Travis | | A61M 5/16804 |
| | | | | 604/500 |
| 2013/0177455 A1 * | 7/2013 | Kamen | | G06F 19/3418 |
| | | | | 417/313 |
| 2013/0211323 A1 * | 8/2013 | Lee | | A61M 5/14228 |
| | | | | 604/67 |
| 2014/0100526 A1 * | 4/2014 | Ueda | | A61M 5/142 |
| | | | | 604/151 |
| 2014/0112828 A1 * | 4/2014 | Grant | | A61M 1/3652 |
| | | | | 422/44 |
| 2015/0285404 A1 * | 10/2015 | Koyama | | F04B 43/12 |
| | | | | 248/74.2 |

* cited by examiner

INFUSION PUMP

BACKGROUND

1. Technical Field

The present invention relates to an infusion pump for forcibly transferring liquid in an infusion tube by pressing the infusion tube radially.

2. Description of the Related Art

Examples of known techniques of this kind include, such as those described in JP-A-2016-59535, an infusion pump device that operates as follows. That is, with the infusion pump device, an infusion tube (10) with its flow path closed by a roller clamp (11) is set in an accommodation portion (20) of an infusion pump device (2), and a door (21) is closed. Then, the flow path is released by operation of the roller clamp (11), and the pump finger (20b) is driven so that a medical fluid and/or the like flows through the infusion tube (10). Note that the numerals in the parentheses above correspond to the reference signs described in JP-A-2016-59535.

SUMMARY

Incidentally, each of the operations of closing and releasing the tube by use of the roller clamp (11) is performed manually outside the infusion pump device (2). This may lead to unintentional free flow due to misoperation and/or the like.

Further, while the door (21) is closed, flowing of the liquid in the infusion tube (1) is sensed by a pressure sensor (22). During the sensing, the door (21) is locked by a latch (23e), which is driven by a solenoid. However, there is a possibility that the door (21) may be opened while the liquid is flowing, due to malfunction of the pressure sensor (22), poor operation of the latch (23e), and/or the like.

In view of these problems, an infusion pump according to an embodiment of the present invention includes a pump body including a tube attachment portion to which an infusion tube is to be attached detachably, and a door pivotably supported by the pump body so that the tube attachment portion is openable and closable by the door. Further, the pump body includes a clamp attachment portion into which a sliding clamp is to be inserted and set, the sliding clamp being configured to close or release the infusion tube by moving in a direction intersecting with the infusion tube, and a release operator configured to be operated in the clamp attachment portion in order to transfer the sliding clamp from a close mode to a release mode. Further, the release operator is configured to be locked, in response to opening movement of the door, so that the release operator is inoperable for releasing, and the release operator is configured to be unlocked in response to closing movement of the door.

DESCRIPTION OF THE EMBODIMENTS

According to a first feature of an embodiment of the present invention, an infusion pump includes: a pump body including a tube attachment portion to which an infusion tube is to be attached detachably; and a door pivotably supported by the pump body so that the tube attachment portion is openable and closable by the door. The pump body includes: a clamp attachment portion into which a sliding clamp is to be inserted and set, the sliding clamp being configured to close or release the infusion tube by moving in a direction intersecting with the infusion tube; and a release operator configured to be operated in the clamp attachment portion in order to transfer the sliding clamp from a close mode to a release mode. The release operator is configured to be locked, in response to opening movement of the door, so that the release operator is inoperable for releasing, and is configured to be unlocked in response to closing movement of the door.

According to a second feature of the present embodiment, the infusion pump may include, in addition to the first feature, an engagement-disengagement member configured to move between a lock position and an unlock position, the lock position causing the engagement-disengagement member to be engaged with the release operator for locking the release operator so that the release operator is inoperable for releasing, the unlock position causing the engagement-disengagement member to come apart from the release operator for unlocking the release operator. The engagement-disengagement member is configured to be in the lock position while the door is opened, and to move to the unlock position as a result of coming in sliding contact with the door that is closing (see FIGS. 4 and 5).

According to a third feature of the present embodiment, the infusion pump may be configured such that, in addition to the first or second feature, the release operator is provided in such a manner that the release operator is allowed to be pushed. The pump body includes an interlocking mechanism configured to move, in response to movement of the release operator in a direction in which the release operator is pushed, the sliding clamp in a direction for releasing the infusion tube (see FIGS. 6 to 10).

Figure 7:
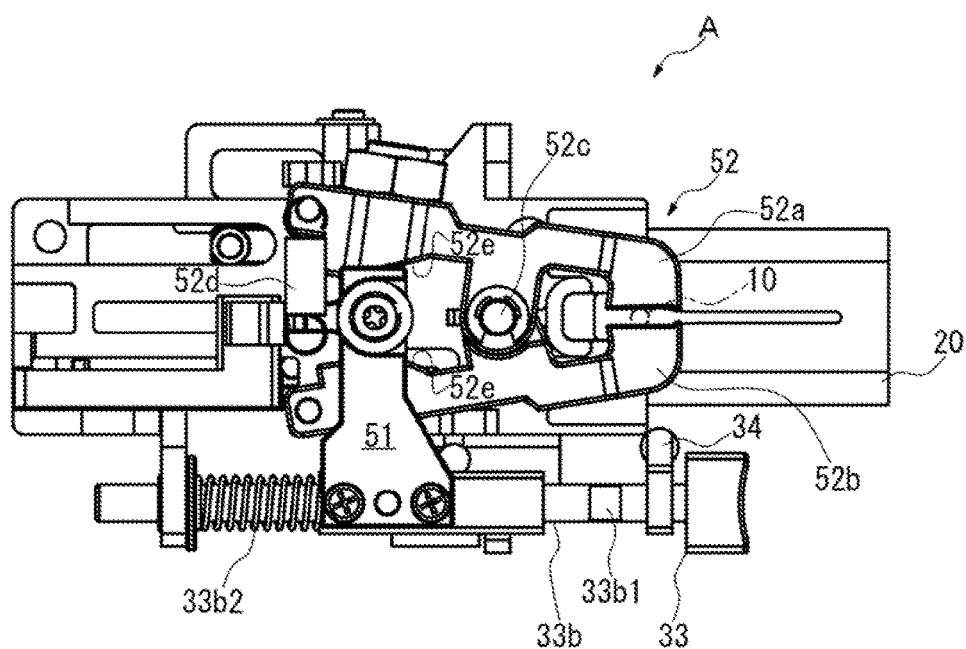
FIG. 7 shows an internal configuration of main components of the infusion pump in which the sliding clamp is moved backward as a result of pushing of the release operator.
Figure 8:
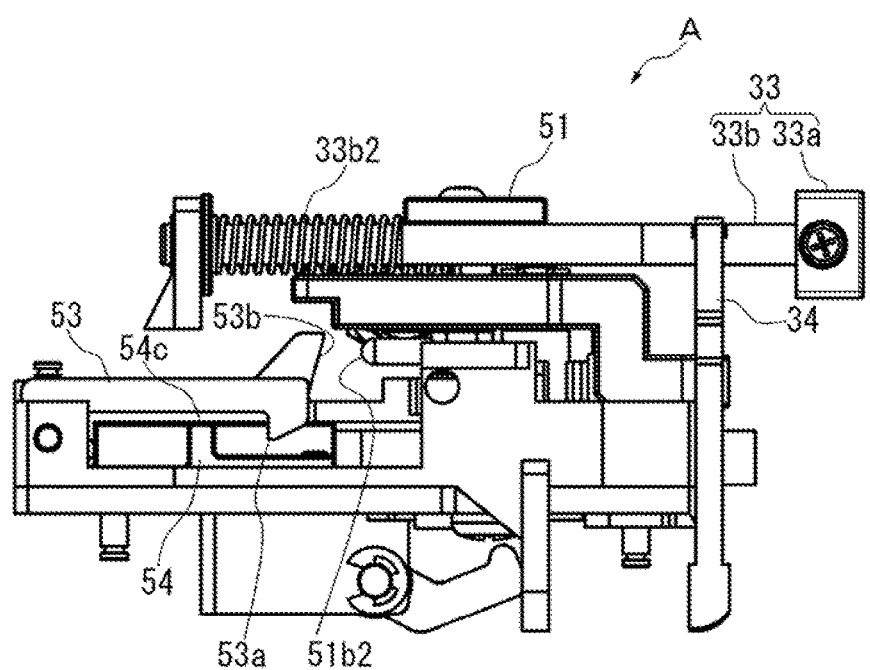
FIG. 8 shows an internal configuration of main components of the infusion pump in FIG. 6 viewed from the bottom, the sliding clamp being set in the infusion pump.

According to a fourth feature of the present embodiment, the infusion pump may be configured such that, in addition to the third feature, the interlocking mechanism includes a holding mechanism configured to hold the infusion tube in response to movement of the release operator in the direction in which the release operator is pushed, and the interlocking mechanism is configured to move the sliding clamp in the direction for the releasing, in a state in which the infusion tube is held by the holding mechanism (see FIG. 7).

According to a fifth feature of the present embodiment, the infusion pump may be configured such that, in addition to any one of the first to fourth features, the clamp attachment portion is configured to hold the sliding clamp inserted thereinto, in such a manner that the sliding clamp is allowed to be pushed. The pump body includes a latch mechanism configured to be locked in response to closing of the door, and to be unlocked in response to pushing of the sliding clamp (see FIGS. 11 and 12).

According to a sixth feature of the present embodiment, the infusion pump may be configured such that, in addition to any one of the first to fifth features, the pump body includes a valve mechanism configured to be opened and closed by respective states of the infusion tube attached to the tube attachment portion, the states including a state in which the infusion tube attached to the tube attachment portion is not pressed from a radially outer side, and a state in which the infusion tube attached to the tube attachment portion is pressed from the radially outer side. The valve mechanism is configured to be closed in response to closing movement of the door, and to be opened in response to opening movement of the door.

<Specific Embodiments>

Next, with reference to the drawings, the following provides detailed descriptions of a specific embodiment having the features described above.

Figure 1:
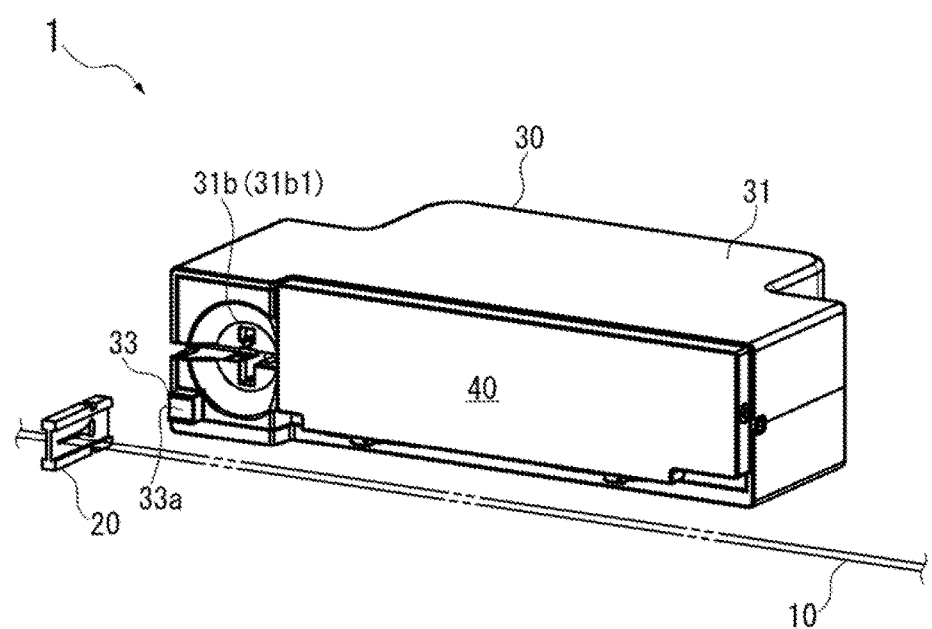
FIG. 1 is a perspective view illustrating one example of an infusion pump according to an embodiment of the present invention.
Figure 2:
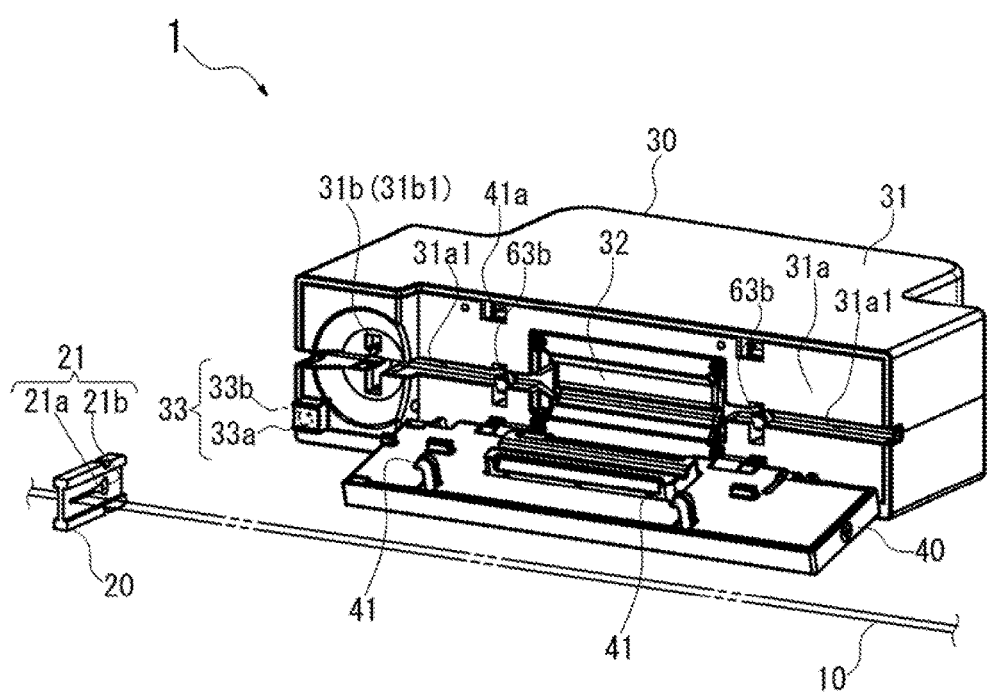
FIG. 2 is a perspective view illustrating the infusion pump with its door opened.

An infusion pump 1 according to the present embodiment includes an infusion tube 10 that is elastically deformable, a sliding clamp 20 being configured to close the infusion tube 10 by moving in one direction intersecting with the infusion tube 10 so that the sliding clamp 20 pinches the infusion tube 10, and being configured to release the infusion tube 10 by moving in a direction opposite to the one direction, a pump body 30 including a tube attachment portion 31a to which the infusion tube 10 is detachably attached, and a door 40 being pivotably supported by the pump body 30 so that the tube attachment portion 31a is openable and closable by the door 40 (see FIGS. 1 and 2).

The infusion tube 10 is a round pipe-shaped tube that is made of a transparent synthetic resin and is elastically deformable radially. When a radial pressing force is applied to the infusion tube 10, the infusion tube 10 is elastically deformed as if the infusion tube 10 is squashed, so that inner surfaces of a portion to which the pressing force is applied are brought into contact with each other, and consequently the portion is closed. Meanwhile, when the pressing force is released, the infusion tube 10 returns to its original shape by an elastic restoring force.

The sliding clamp 20 is a flat board-shaped member having a tube insertion hole 21 through which the infusion tube 10 is inserted. In the example shown in the drawings, the sliding clamp 20 is shaped in a rectangular flat board.

The tube insertion hole 21 has a small width portion 21a whose width is set to be smaller than twice a wall thickness of the infusion tube 10 and a large width portion 21b whose width is set to be larger than an outer diameter of the infusion tube 10. Further, the tube insertion hole 21 has, between the small width portion 21a and the large width portion 21b, a gradually changing height.

Thus, by setting the tube insertion hole 21 for the infusion tube 10 so that the tube insertion hole 21 surrounds the infusion tube 10 and moving the small width portion 21a toward an outer surface of the infusion tube 10, the infusion tube 10 is pinched by the small width portion 21a, so that an internal flow path of the infusion tube 10 is closed. Meanwhile, by moving the large width portion 21b toward the outer surface of the infusion tube 10, the infusion tube 10 returns to its original shape by an elastic restoring force, so that the internal flow path is released.

The pump body 30 includes a case 31 including the tube attachment portion 31a and a clamp attachment portion 31b, a pump mechanism 32 configured to forcibly transfer liquid in the infusion tube 10 attached to the tube attachment portion 31a, a release operator 33 configured to be operated for transferring the sliding clamp 20 that is attached to the clamp attachment portion 31b from a close mode to a release mode, an engagement-disengagement member 34 (see FIGS. 4 and 5) configured to be engaged with or disengaged from the release operator 33, an interlocking mechanism A (see FIGS. 6 to 10) configured to move, in response to movement of the release operator 33 in a direction in which the release operator 33 is pushed, the sliding clamp 20 in a direction for releasing the infusion tube 10, a latch mechanism B (see FIGS. 11 and 12) configured to be locked in response to closing of the door 40, and a valve mechanism C (see FIGS. 16 to 18) configured to press, from a radially outer side, the infusion tube 10 attached to the tube attachment portion 31a for closing the infusion tube 10.

As shown in FIGS. 1 and 2, the case 31 has a substantially box-shape. The case 31 has a front side including the tube attachment portion 31a and the clamp attachment portion 31b that are disposed side by side.

The tube attachment portion 31a is, in the front side of the case 31, covered by the door 40 in such a manner that the tube attachment portion 31a is openable and closable by the door 40.

The tube attachment portion 31a has, in a portion close to its center in a horizontal width direction, a pump mechanism 32. Further, the pump mechanism 32 has both ends horizontally continued to respective tube insertion grooves 31a1.

The clamp attachment portion 31b is provided in the path of one (the left one in FIG. 2) of the tube insertion grooves 31a1.

Figure 3:
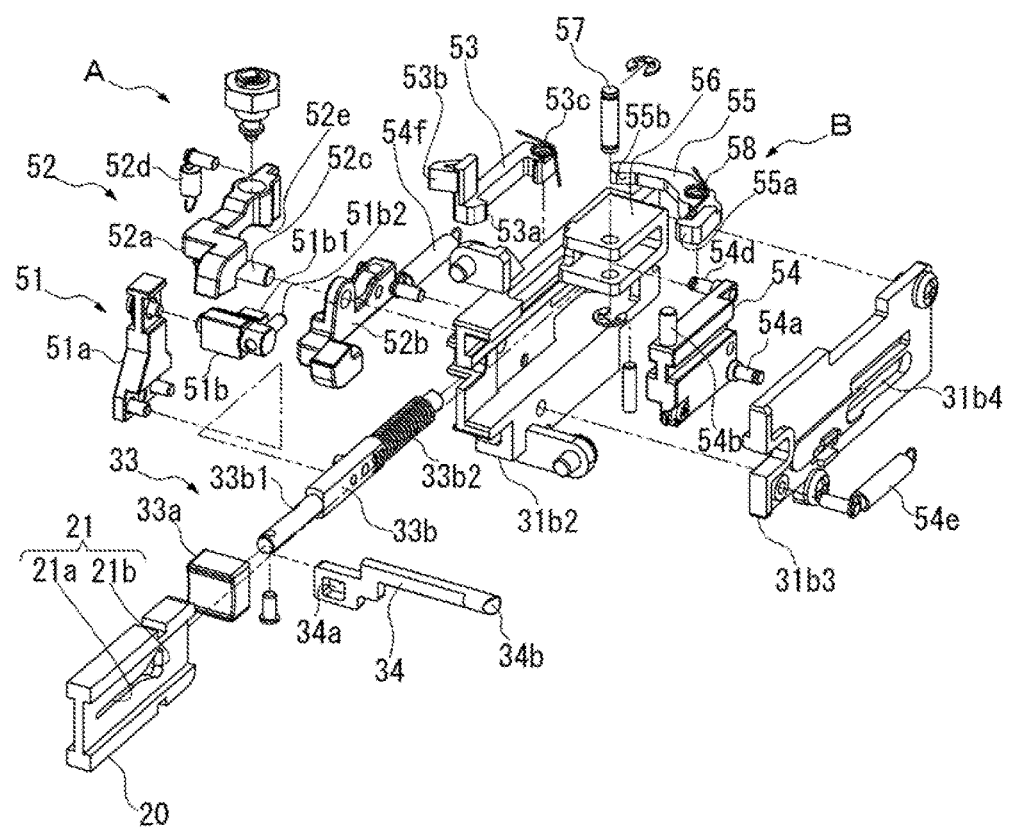
FIG. 3 is an exploded perspective view of main components of the infusion pump, illustrating features of the embodiment of the present invention.

The clamp attachment portion 31b includes an opening 31b1 (see FIGS. 1 and 2) and a support base 31b2 (see FIG. 3). Through the opening 31b1, the sliding clamp 20 having the infusion tube 10 set therein is inserted as a result of moving in a direction for pinching the infusion tube 10. The support base 31b2 is configured to guide, in the opening 31b1, the sliding clamp 20 so that the sliding clamp 20 moves to a back side. The support base 31b2 is fixed on the case 31, and is covered with a cover member 31b3 such that a clamp slider 54 (described later) is interposed between the support base 31b2 and the cover member 31b3 and the clamp slider 54 is movable forward and backward.

Further, the clamp attachment portion 31b holds the sliding clamp 20 inserted thereinto, in such a manner that the sliding clamp 20 protrudes from the case 31 so as to allow the sliding clamp 20 to be pushed.

As those disclosed by, e.g., JP-A-2007-23803 and WO 2014/123178 A, the pump mechanism 32 forcibly transfers liquid in the infusion tube 10 by suitably combining operations of pressing and releasing the infusion tube 10 set therein with operations of opening and closing valves 63b respectively provided upstream and downstream of the pump mechanism 32.

The release operator 33 includes a push-button 33a at one end of the release operator 33, and a sliding shaft 33b connected with the push-button 33a and inserted in the case 31.

The release operator 33 has a portion close to the push-button 33a, the portion being exposed to the outside of the pump body 30 so that the release operator 33 is allowed to be pushed.

The sliding shaft 33b is a long, substantially-cylindrical member (see FIG. 3). The sliding shaft 33b has a front portion (a portion close to the push-button 33a) including a recess 33b1 configured to be engaged with and disengaged from an engagement-disengagement member 34 (described later).

Further, the sliding shaft 33b has a portion close to the back side, the portion including an urging member 33b2 (a compression spring in the example shown in the drawings) attached to the sliding shaft 33b annularly. The urging member 33b2 has one end fastened to the support base 31b2 and the other end fastened to the sliding shaft 33b, and urges the sliding shaft 33b frontward.

The release operator 33, which operates via the engagement-disengagement member 34, is configured to be locked in response to opening movement of the door 40, and to be unlocked in response to closing movement of the door 40.

The engagement-disengagement member 34 is shaped in a horizontally-long bar. The engagement-disengagement member 34 has one end having an engagement hole 34a and the other end having a cam slant surface 34b. The engagement hole 34a allows the sliding shaft 33b to be inserted thereinto, and the engagement hole 34a is configured to be engaged with the recess 33b1 of the sliding shaft 33b. The cam slant surface 34b is configured to come in sliding contact with the door 40 that is closing.

Figure 4:
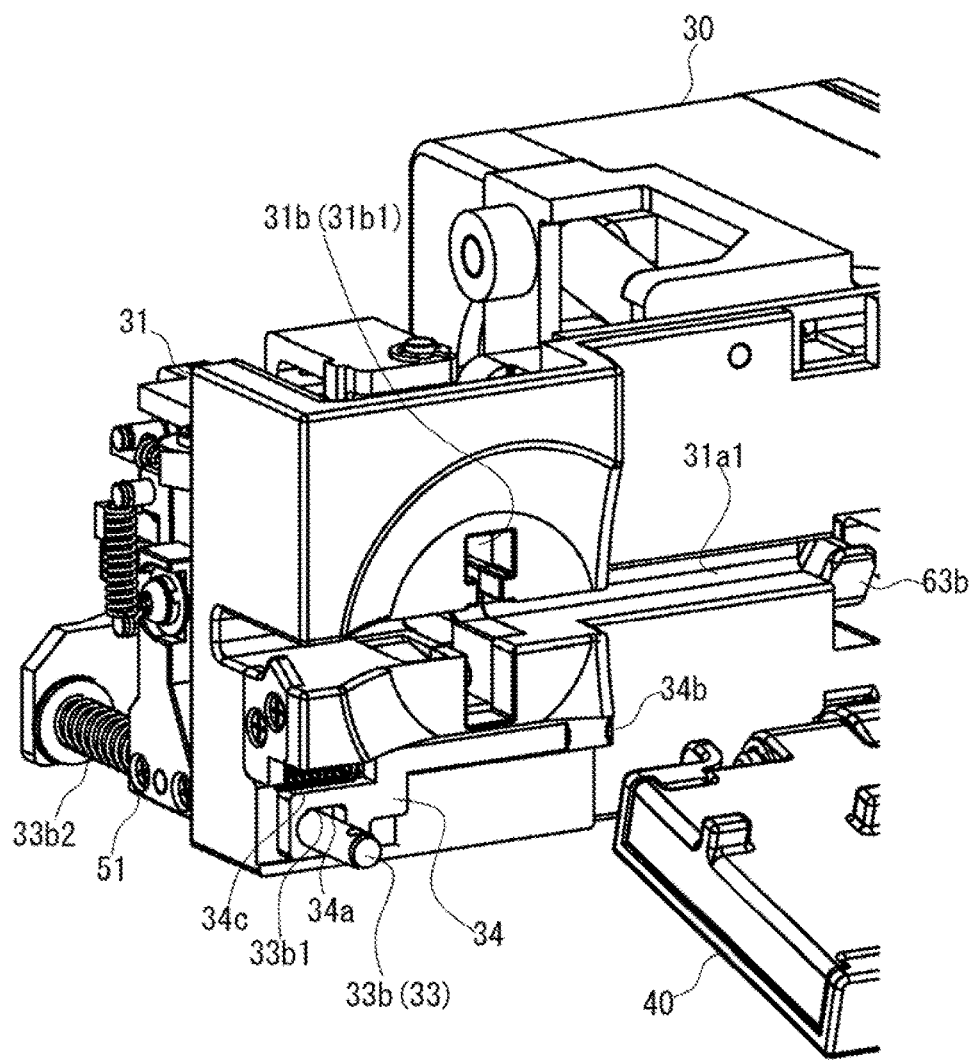
FIG. 4 is a partially cutaway, enlarged perspective view illustrating an internal configuration of the infusion pump in which a release operator is locked.

As shown in FIG. 4, when the door 40 is opened, the engagement-disengagement member 34 is urged toward the door 40 by one end of an urging member 34c (a compression spring in the example shown in the drawings) having the other end fastened to the case 31, and then an inner periphery of the engagement hole 34a is engaged with the recess 33b1 of the sliding shaft 33b. Consequently, the engagement-disengagement member 34 is brought to a lock position for locking the release operator 33 in such a manner that the release operator 33 is inoperable.

Meanwhile, when the door 40 moves for closing, the cam slant surface 34b comes in sliding contact with the door 40 that is closing, so that the engagement-disengagement member 34 moves to come apart from the door 40. Consequently, the inner periphery of the engagement hole 34a comes apart from the recess 33b1 of the sliding shaft 33b, and thus the engagement-disengagement member 34 is brought to an unlock position for unlocking the locked state with respect to the release operator 33 (see FIG. 5).

Further, the interlocking mechanism A includes an interlocking member 51, a holding mechanism 52, a slider locking member 53, and a clamp slider 54. The interlocking member 51 is coupled to the release operator 33. The holding mechanism 52 is configured to hold the infusion tube 10 as a result of engagement with the interlocking member 51 and movement in response to movement of the release operator 33 in a direction in which the release operator 33 is pushed. The slider locking member 53 is configured to come in sliding contact with the interlocking member 51, so that the slider locking member 53 moves rotatably. The clamp slider 54 is fastened to the slider locking member 53 (see FIG. 3).

Figure 6:
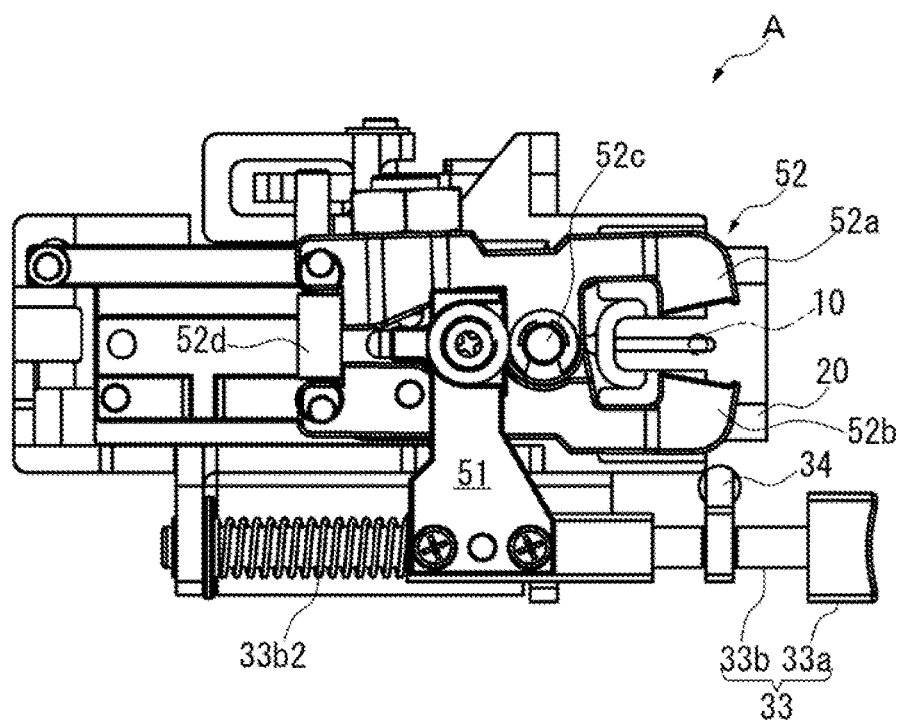
FIG. 6 shows an internal configuration of main components of the infusion pump in which the sliding clamp is set.

The interlocking member 51 has one end being connected with the release operator 33 and the other end extending in a direction intersecting with the release operator 33 (see FIG. 6). Further, the interlocking member 51 has a portion close to the other end in the extending direction, the portion including an operation projection 51b1 configured to open and close the holding mechanism 52 and an unlock projection 51b2 configured to unlock the slider locking member 53 (see FIG. 3).

In the example shown in the drawings, the interlocking member 51 is constituted by two members, that is, a connection piece 51a connected with the sliding shaft 33b and an operation piece 51b connected with the connection piece 51a.

The holding mechanism 52 pivotably supports one piece 52a and the other piece 52b in such a manner that a space between front ends of the one piece 52a and the other piece 52b is reduced when a space between back ends of the one piece 52a and the other piece 52b is increased. Further, the holding mechanism 52 includes an urging member 52d (a tension spring in the example shown in the drawings) configured to pull the back ends of the one piece 52a and the other piece 52b so that these back ends are located to be closer to the back side than the pivot 52c is. Furthermore, the pivot 52c of the holding mechanism 52 is supported by the support base 31b2.

Further, the one piece 52a and the other piece 52b have respective cam slant surfaces 52e (see FIG. 7) located to be closer to the back side than the pivot 52c is, the cam slant surfaces 52e being configured to come in sliding contact with the operation projection 51b1.

With the holding mechanism 52, the cam slant surfaces 52e come in sliding contact with the operation projection 51b1 of the interlocking member 51, so that the space between the back sides of the one piece 52a and the other piece 52b is increased against an urging force by the urging member 52d, and thereby the space between the front ends of the one piece 52a and the other piece 52b is reduced.

Consequently, the infusion tube 10 is pinched in the space thus reduced (see FIGS. 6 and 7).

Further, the slider locking member 53 is configured to lock the clamp slider 54 pushed by the sliding clamp 20 inserted in the clamp attachment portion 31b, in such a manner that the clamp slider 54 is immovable backward, and is configured to unlock the locked state (see FIGS. 3 and 8 to 10).

The slider locking member 53 has one end toward which the sliding clamp 20 is inserted, the one end being pivotably supported by the support base 31b2. Further, the slider locking member 53 has, in an end opposite to the one end, a claw 53a configured to lock the clamp slider 54 in such a manner that the clamp slider 54 is immovable backward, and a cam slant surface 53b configured to come in sliding contact with the unlock projection 51b2 (see FIGS. 8 to 10).

Further, the slider locking member 53 includes, in the portion at which the sliding clamp 20 is pivotably supported, an urging member 53c (a torsion spring in the example shown in FIG. 3) configured to urge the slider locking member 53 in a direction for locking.

According to the slider locking member 53, the claw 53a is usually engaged with the clamp slider 54 so that the clamp slider 54 is immovable backward. When the release operator 33 is pushed, the unlock projection 51b2 of the interlocking member 51, which moves in an unified manner with the release operator 33, comes in sliding contact with the claw 53a, so that the claw 53a is moved rotatably to come apart from the clamp slider 54. Consequently, the locked state with respect to the clamp slider 54 is unlocked (see FIGS. 8 to 10).

The claw 53a has a substantially hook-shape. The claw 53a has an inner surface configured to be engaged with an engagement projection 54c of the clamp slider 54 (described later). Further, the claw 53a has an outer slant surface configured to allow, when the clamp slider 54 moves in the direction of pushing, the engagement projection 54c of the clamp slider 54 to slide onto the outer slant surface and go over the claw 53a.

The clamp slider 54 is supported in the support base 31b2 in such a manner that the clamp slider 54 is movable forward and backward while in contact with the sliding clamp 20 in the clamp attachment portion 31b.

The clamp slider 54 has the engagement projection 54c (see FIGS. 13 and 14) configured to be engaged with the claw 53a of the slider locking member 53.

When the clamp slider 54 moves toward the inside of the pump body 30, the engagement projection 54c comes in sliding contact with the outer slant surface of the claw 53a of the slider locking member 53, so that the engagement projection 54c pushes aside the slider locking member 53 and thereby the slider locking member 53 is moved rotatably. Consequently, the engagement projection 54c is engaged with the inner surface of the claw 53a (see FIGS. 13 to 15).

The clamp slider 54 has a pin 54a fixed thereon in such a manner that the pin 54a penetrates through a long hole 31b4 extending in a front-back direction of the cover member 31b3 (see FIG. 3). The pin 54a is fixed at one end of an urging member 54e (a tension spring in the example shown in the drawings) having the other end fixed at the cover member 31b3.

The clamp slider 54 has a side opposite to a direction in which the pin 54a protrudes, the side having a pin 54d (see FIG. 3) provided thereon. The pin 54d is fixed at one end of an urging member 54f (a tension spring in the example shown in the drawings) having the other end fixed at the other piece 52b.

Thus, the clamp slider 54 is urged by the two urging members 54e and 54f in a direction opposite to a direction in which the sliding clamp 20 is pushed.

Further, the clamp slider 54 has a pin 54b (see FIG. 3) fixed thereon, the pin 54b being configured to push a link member 55 (described later). The pin 54b protrudes upward, and has an outer surface configured to push the link member 55 (described later) (see FIGS. 11 and 12).

The latch mechanism B is configured to be locked in response to closing of the door 40, and to be unlocked in response to pushing of the sliding clamp 20 (see FIGS. 11 to 15).

Figure 11:
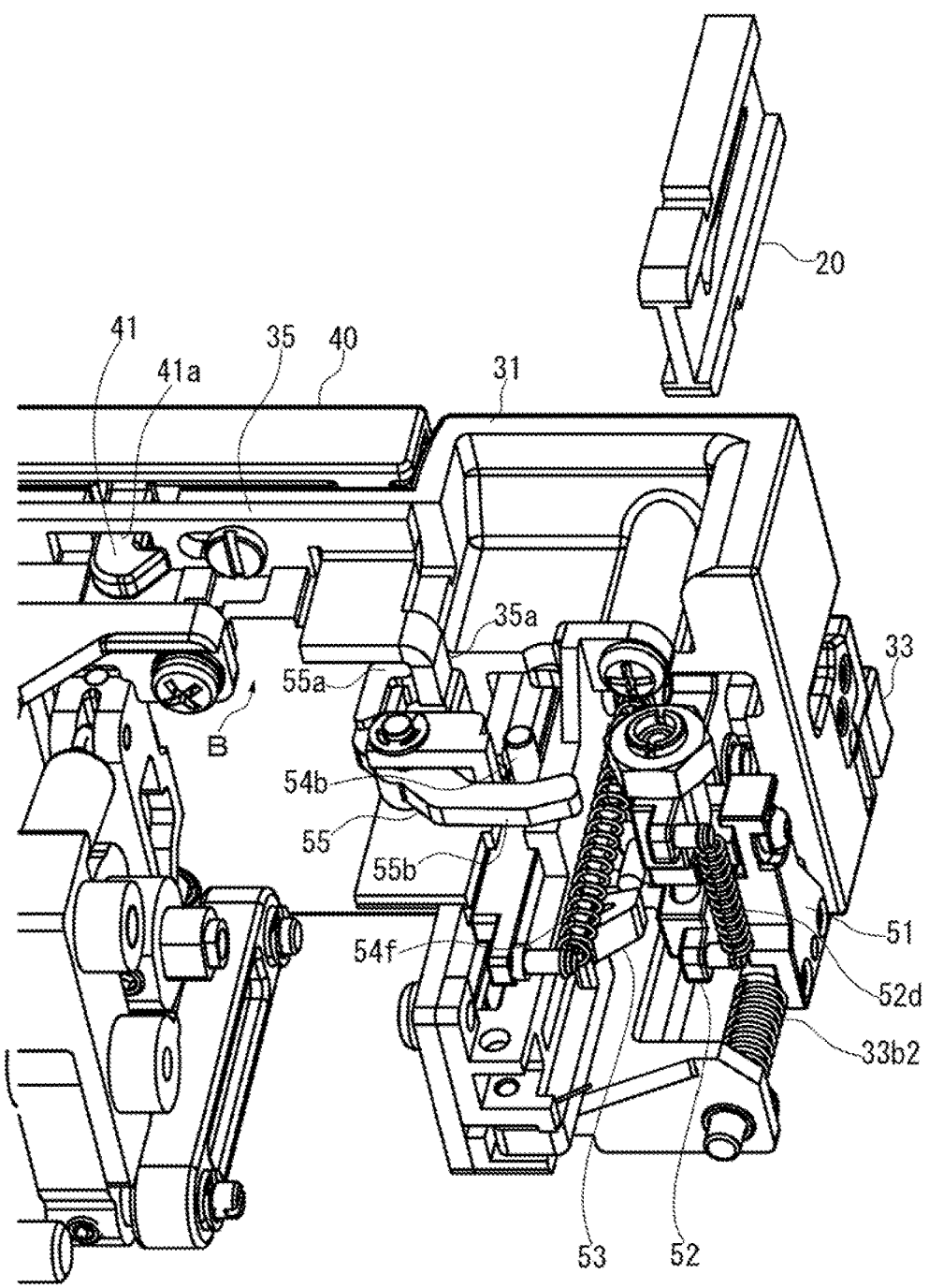
FIG. 11 shows an internal configuration of main components of the infusion pump in which the sliding clamp is not attached yet, viewed from a back side and obliquely above.
Figure 12:
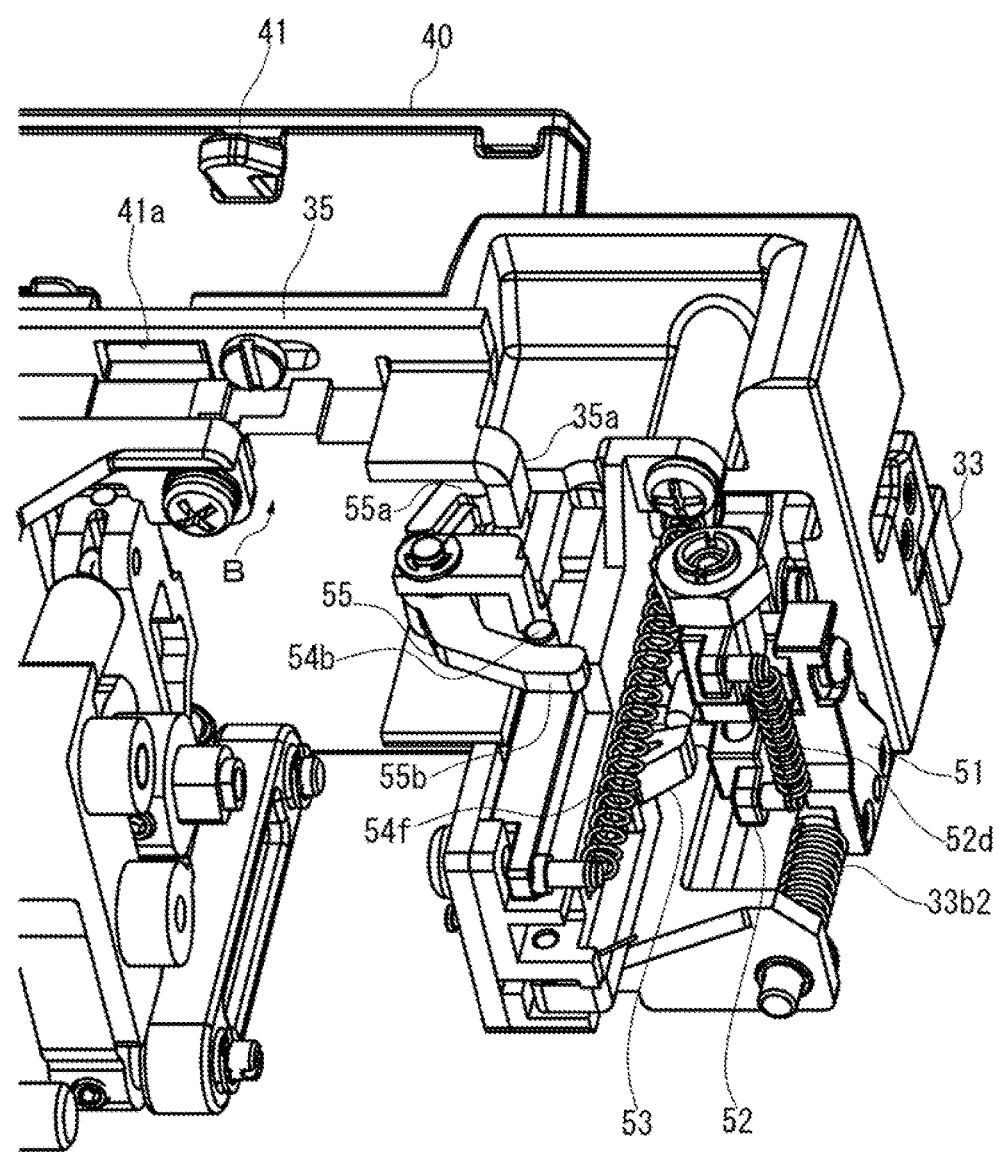
FIG. 12 shows an internal configuration of main components of the infusion pump in which the sliding clamp is attached, viewed from a back side and obliquely above.

Specifically, the latch mechanism B includes latches 41 fixed on a back surface of the door 40, an engagement-disengagement piece 35 provided in the pump body 30 and configured to slide so as to be engaged with and disengaged from the latches 41, and the link member 55 configured to cause, in response to pushing of the sliding clamp 20, the engagement-disengagement piece 35 to slide in a direction for disengaging the engagement-disengagement piece 35 from the latches 41 (see FIGS. 11 and 12).

The latches 41 each have a tip end shaped in a hook facing sideways. While the door 40 is closed, the latches 41 are inserted into respective cutouts in a front wall of the case 31 so that the latches 41 penetrate through the cutouts, and the hook-shaped tip ends are engaged with the engagement-disengagement piece 35 (see FIG. 11).

The engagement-disengagement piece 35 has engagement-disengagement holes 41a configured to allow the tip ends of the latches 41 to be inserted through the engagement-disengagement holes 41a and to be engaged with and disengaged from the engagement-disengagement holes 41a, respectively. Further, the engagement-disengagement piece 35 is supported by a back surface of a front wall of the case 31 in such a manner that the engagement-disengagement piece 35 is slidable laterally (see FIGS. 11 and 12).

The engagement-disengagement piece 35 has a receiving portion 35a configured to receive a tip end of the link member 55.

Further, the engagement-disengagement piece 35 is urged, by an urging member (for example, a compression spring or a tension spring) which is not illustrated in the drawings, in a direction (leftward in FIG. 11) for causing the engagement-disengagement holes 41a to be disengaged from the latches 41.

The link member 55 is shaped in a curved piece (see FIG. 3). The link member 55 has one end having a pressing projection 55a configured to press the receiving portion 35a of the engagement-disengagement piece 35 (see FIG. 11), and the other end having a pressed portion 55b configured to be pressed by the upwardly protruded pin 54b of the clamp slider 54. Further, the link member 55 has a portion interposed between the pressing projection 55a and the pressed portion 55b, the portion being pivotably supported by the support base 31b2 via, e.g., a support bracket 56 and a shaft member 57, in such a manner that the link member 55 is rotatable at a predetermined angle. Furthermore, the link member 55 is urged by an urging member (a torsion spring in the example shown in the drawings) in a rotational direction for causing the pressing projection 55a to come apart from the receiving portion 35a.

Thus, with the latch mechanism B, when the pressed portion 55b of the link member 55 is pressed by the pin 54b of the clamp slider 54, a force of the pressing causes the link member 55 to be rotated by a predetermined amount, so that the pressing projection 55a of the link member 55 presses the receiving portion 35a of the engagement-disengagement piece 35. This causes the engagement-disengagement piece 35 to slide so that the engagement-disengagement piece 35 is disengaged from the latches 41, and consequently the door 40 is made openable.

Figure 16:
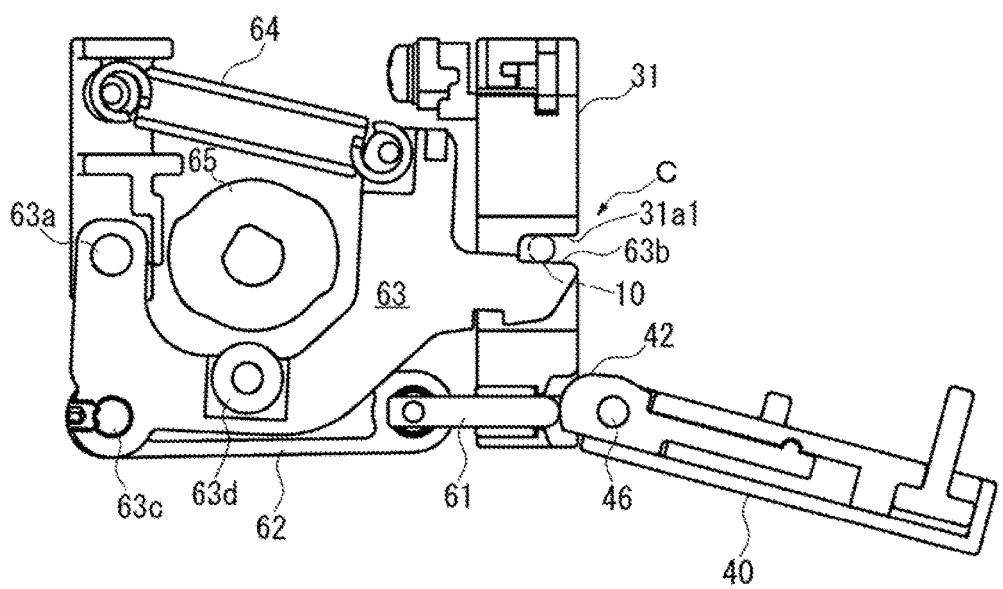
FIG. 16 shows an internal configuration of main components of the infusion pump in which the door is opened and a valve member is opened, viewed from a lateral side.
Figure 17:
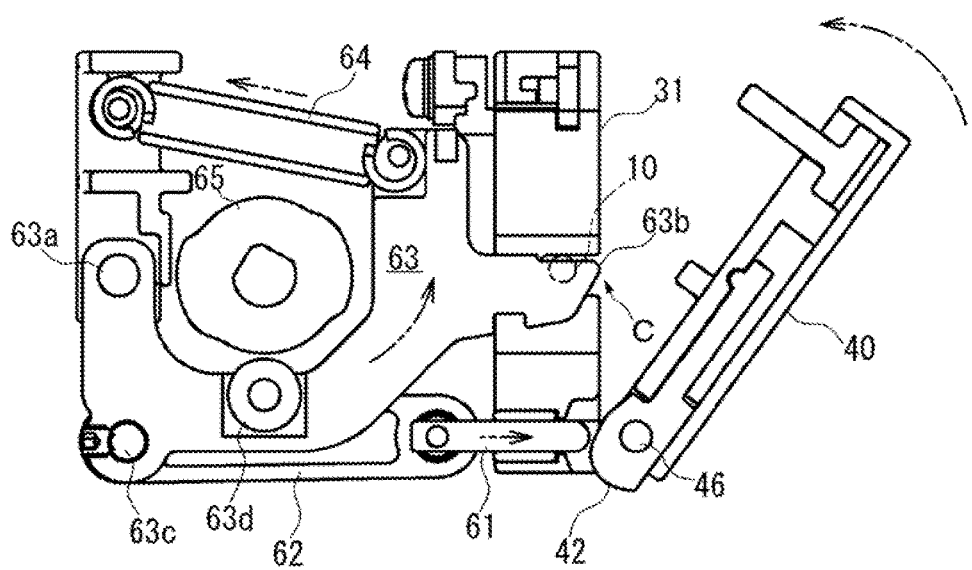
FIG. 17 shows an internal configuration of main components of the infusion pump in which the door is closed halfway and the valve member is closed, viewed from a lateral side.
Figure 18:
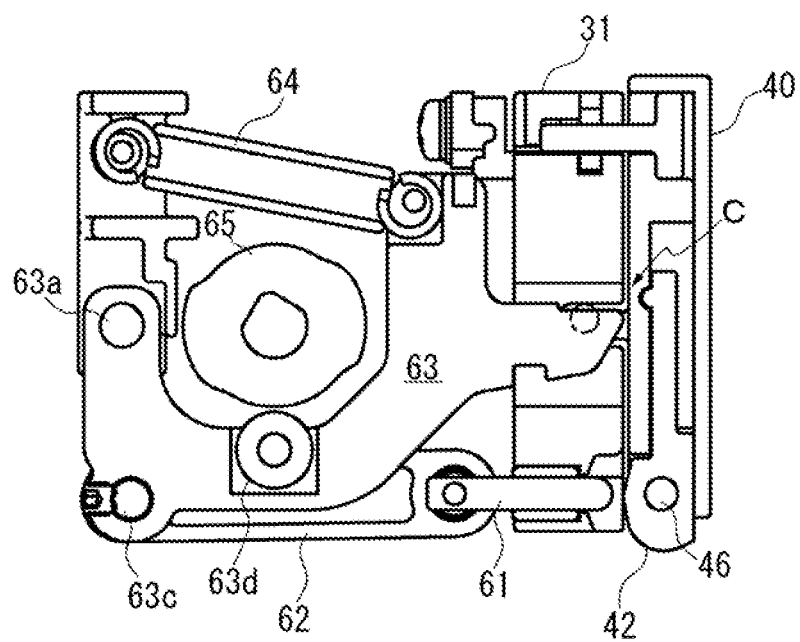
FIG. 18 shows an internal configuration of main components of the infusion pump in which the door is fully closed and the valve member is closed, viewed from a lateral side.

As shown in FIGS. 16 to 18, the valve mechanism C includes a cam portion 42 fixed around a rotational shaft 46 of the door 40 so as to be rotatable in a unified manner with the rotational shaft 46, a sliding member 61 configured to come in sliding contact with the cam portion 42 so as to slide linearly, a transmitting member 62 configured to move linearly in a unified manner with the sliding member 61, and a valve member 63 configured to rotate by a predetermined amount in response to movement of the transmitting member 62 so as to open and close the valves 63b.

The cam portion 42 has an outer surface that is curved with a changing radius with respect to the center of the rotational shaft 46 of the door 40, the outer surface being configured to come in sliding contact with the sliding member 61.

The sliding member 61 has a substantially shaft-shape, and is provided so as to be slidable forward and backward by a predetermined amount inside the pump body 30.

The transmitting member 62 is interposed between the sliding member 61 and the valve member 63 and is connected with the sliding member 61 and the valve member 63. Further, the transmitting member 62 is configured to transmit a front-back direction force of the sliding member 61 to the valve member 63 (described later). The transmitting member 62 may be integrated with the sliding member 61.

While the door 40 is closing from a fully-opened state, the sliding member 61 operates as follows. That is, in a first half of the closing, the sliding member 61 slides toward the outside of the pump body 30 (rightward in the drawings) by an urging force by an urging member 64 (see FIGS. 16 and 17). Then, in a latter half of the closing, the sliding member 61 comes apart from the door 40 (see FIGS. 17 and 18).

Meanwhile, while the door 40 is opening from a fully-closed state, the sliding member 61 operates in a manner reverse to the above-described manner That is, in a latter half of the opening, the sliding member 61 comes in sliding contact with the cam portion 42, so that the sliding member 61 slides toward the inside of the pump body 30 (leftward in the drawings).

The valve member 63 is supported, in the pump body 30, by a rotational shaft 63a disposed at one end of the valve member 63 in such a manner that the valves 63bdisposed at the other end of the valve member 63 is rotatable about the rotational shaft 63a by a predetermined amount. Further, in the example shown in FIGS. 16 to 18, the valve member 63 has a substantially concaved shape in a side view.

The valves 63b are configured to open and close a space between the valves 63b and an inner surface of the tube insertion grooves 31a1 in the case 31, so that the infusion tube 10 elastically deforms radially and thus the infusion tube 10 opens and closes.

The valve member 63 has a portion close to an outer surface of the rotational shaft 63a, the portion including a pivot 63c for the valve member 63 and the transmitting member 62. While the door 40 is closing, the valve member 63 causes the valves 63b to be closed by an urging force by the urging member 64 (see FIGS. 16 to 18). Meanwhile, while the door 40 is opening, the valve member 63 causes the valves 63b to be opened by a force transmitted by, e.g., the cam portion 42, the sliding member 61, and the transmitting member 62.

When the pump mechanism 32 is driven while the door 40 is closed, a cam member 65 provided in the vicinity of a center of the valve member 63 is rotated, so that a projection and a recess on an outer surface of the cam member 65 are engaged with and disengaged from a roller 63d, which is supported by the valve member 63. Accordingly, the valve member 63 is moved rotatably by a predetermined amount, so that the valves 63b are opened and closed repeatedly at a suitably timing.

Next, the following provides details of characteristic effects given by the infusion pump 1 configured as above.

First, as a preparation before use of the infusion pump 1, the sliding clamp 20 is set for the infusion tube 10. Specifically, the sliding clamp 20 is set for the infusion tube 10 so that the sliding clamp 20 surrounds the infusion tube 10, and the small width portion 21a of the sliding clamp 20 is fitted to the infusion tube 10, so that the infusion tube 10 is maintained in a closed state.

Next, the sliding clamp 20 is inserted into the clamp attachment portion 31band is set therein. This unlocks the locked state of the door 40.

As a result of the unlocking of the door 40, the door 40 is opened.

The door 40 is opened widely, and the infusion tube 10 is set in the pump body 30. In this state in which the door 40 is opened, the release operator 33 is locked, and therefore the closed state of the infusion tube 10 by the sliding clamp 20 cannot be released.

Next, after the door 40 is closed, the release operator 33 is pushed so that the closed state of the infusion tube 10 by the sliding clamp 20 is released. In this state, it is possible to operate the infusion pump 1 for liquid feeding.

After the liquid feeding, in order to remove the sliding clamp 20 and the infusion tube 10 from the infusion pump 1, the sliding clamp 20 is pushed so that the infusion tube 10 is closed by the sliding clamp 20 and the door 40 is unlocked.

Then, as shown in FIG. 2, the door 40 is opened widely. Thus, it is possible to remove the sliding clamp 20 and the infusion tube 10 from the infusion pump 1.

The following provides further details of the characteristic effects, starting from the setting of the infusion tube 10 in the pump body 30.

To the pump body 30 with the sliding clamp 20 inserted into the clamp attachment portion 31b and the door 40 opened, the infusion tube 10 is attached.

In the attachment, the infusion tube 10 is fitted to the tube insertion grooves 31a1, the pump mechanism 32, and the like, and penetrates through the case 31 over a full horizontal length of the case 31.

Further, with the infusion tube 10 closed by the sliding clamp 20, the sliding clamp 20 is inserted into the clamp attachment portion 31b. Further, a front portion of the sliding clamp 20 is exposed to the outside of the case 31.

In this state in which the door 40 is opened, as shown in FIG. 4, the engagement-disengagement member 34 is engaged with the recess 33b1 of the sliding shaft 33b, and thus the release operator 33 is in a locked state in which the release operator 33 is inoperable for releasing. This does not allow the release operator 33 to be pushed even if an operator and/or the like presses the release operator 33 by mistake.

Next, while the door 40 is closing from a fully-opened state (see FIG. 16), in the process of the door 40's closing (see FIG. 17), the cam portion 42 provided in the vicinity of a base end of the door 40 comes apart from the sliding member 61. Consequently, the valve member 63 is rotatably moved by an urging force by the urging member 64, so that the valves 63b press the infusion tube 10 and thus the flow path in the infusion tube 10 is closed (see FIG. 18).

Figure 5:
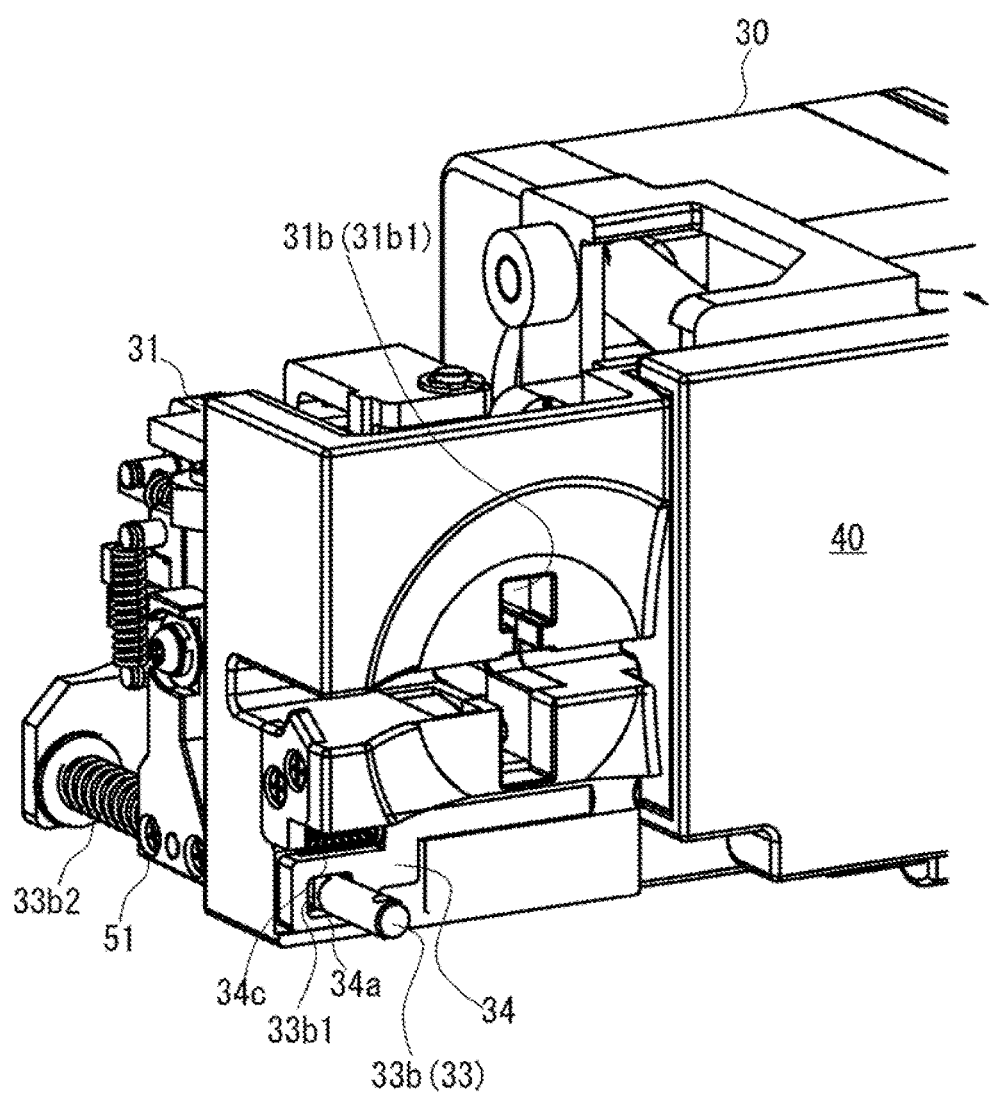
FIG. 5 is a partially cutaway, enlarged perspective view illustrating an internal configuration of the infusion pump in which the release operator is unlocked.

Further, while the door 40 is closing, as shown in FIGS. 4 and 5, the door 40 comes in sliding contact with the cam slant surface 34b in the end of the engagement-disengagement member 34, so that the engagement-disengagement member 34 slides in a direction for causing the engagement-disengagement member 34 to come apart from the door 40 (leftward in FIG. 5). Accordingly, the locked state of the release operator 33 is unlocked. Therefore, while the door 40 is fully closed (see FIG. 5), it is possible for an operator and/or the like to push the release operator 33.

Next, when the release operator 33 is pushed while the door 40 is in a fully-closed state, as shown in FIGS. 6 and 7, the sliding shaft 33b and the interlocking member 51, which slide in response to the pushing, are engaged with the holding mechanism 52. Accordingly, the tip ends of the holding mechanism 52 move for closing, so that the infusion tube 10 is held by the holding mechanism 52 (see FIG. 7).

Figure 9:
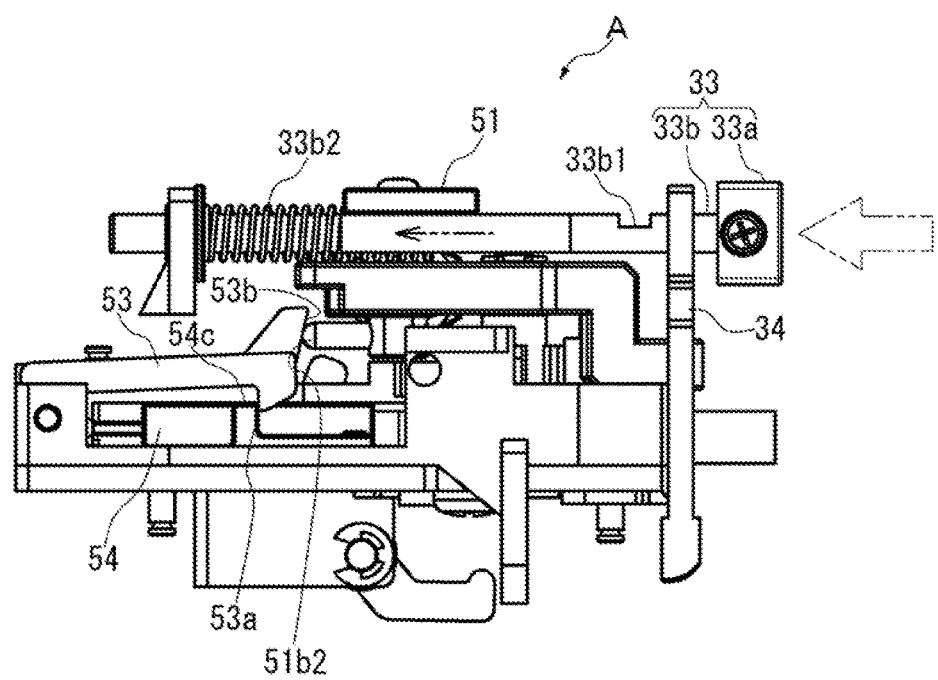
FIG. 9 shows an internal configuration of main components of the infusion pump in which the release operator is pushed halfway.
Figure 10:
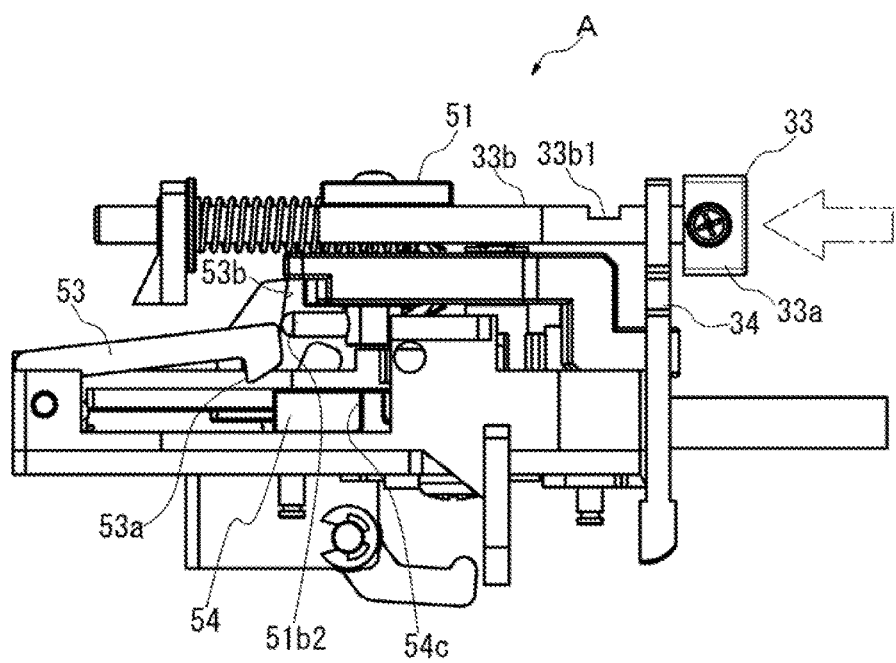
FIG. 10 shows an internal configuration of main components of the infusion pump in which the release operator is pushed and the sliding clamp is moved backward.

Then, after the movement for holding, as shown in FIG. 9, the unlock projection 51b2 of the interlocking member 51 comes in sliding contact with the cam slant surface 53b of the slider locking member 53, so that the claw 53a of the slider locking member 53 is rotatably moved to be disengaged from the engagement projection 54c of the clamp slider 54. Consequently, by urging forces by the urging members 54e and 54f, the slider locking member 53 slides in a direction (rightward in FIG. 9) opposite to the direction in which the release operator 33 is pushed, so that the slider locking member 53 pushes the sliding clamp 20 back toward the outside of the pump body 30. While the sliding clamp 20 is being pushed back, the infusion tube 10 is not pushed back together with the sliding clamp 20, because the infusion tube 10 is held by the holding mechanism 52.

Thus, in the clamp attachment portion 31b, the infusion tube 10 gets out of the small width portion 21a of the sliding clamp 20, so as to be located in the large width portion 21b. This allows the infusion tube 10 to be elastically restored, so as to transfer to an opened state which allows liquid to flow through the infusion tube 10.

Further, when the pump mechanism 32 is driven in the opened state, liquid in the infusion tube 10 is forcibly transferred by a pumping effect given by the pump mechanism 32.

Furthermore, when the sliding clamp 20 is pushed into the pump body 30 after the pump mechanism 32 completes the transferring of the liquid and is stopped, the small width portion 21a of the sliding clamp 20 is attached to the infusion tube 10, so that the inside of the infusion tube 10 is closed.

Figure 13:
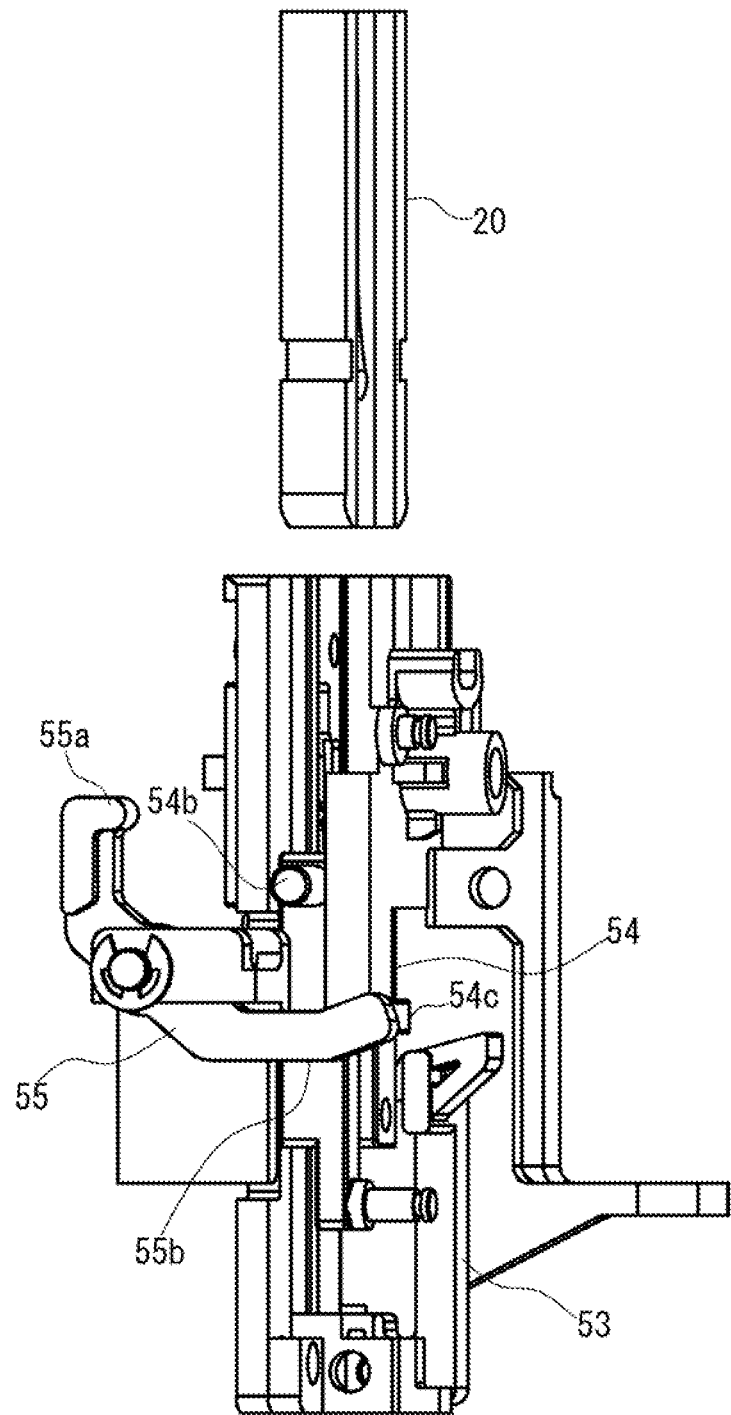
FIG. 13 shows an internal configuration of main components of the infusion pump in which the sliding clamp is not attached yet, viewed from a lateral side and obliquely above the sliding clamp.
Figure 14:
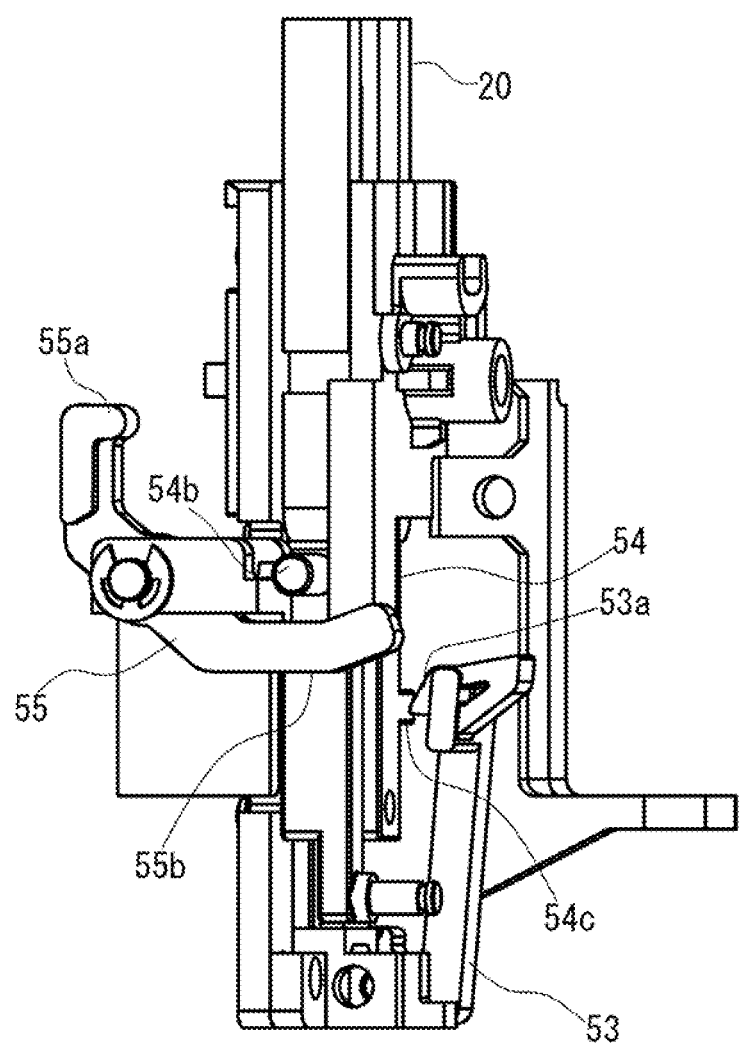
FIG. 14 shows an internal configuration of main components of the infusion pump in which the sliding clamp is attached and is pushed halfway, viewed from a lateral side and obliquely above the sliding clamp.
Figure 15:
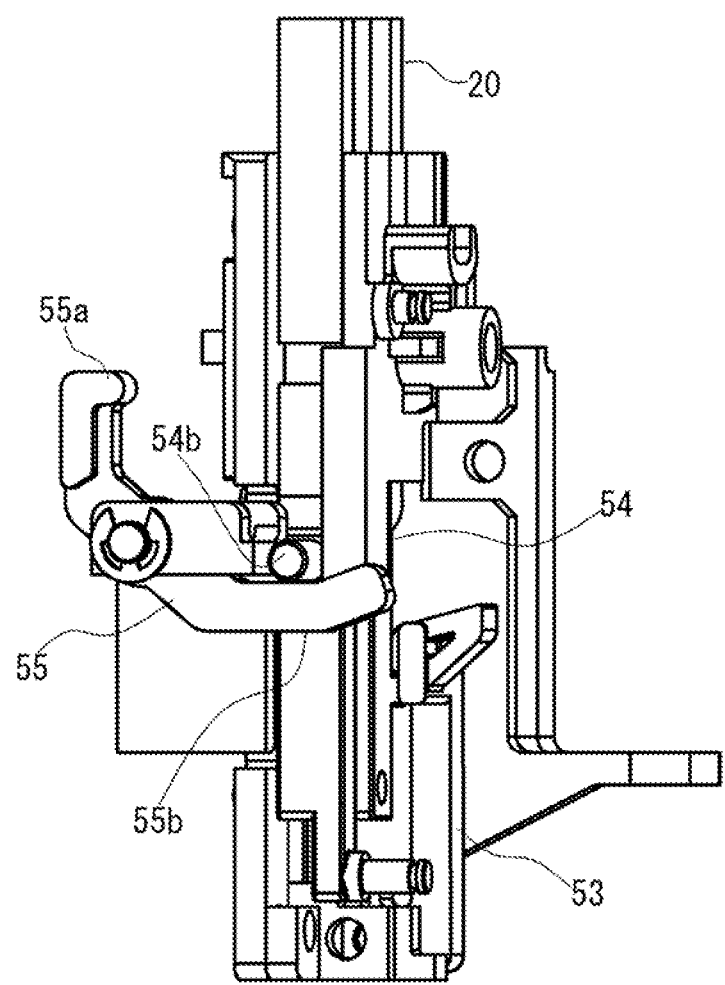
FIG. 15 shows an internal configuration of main components of the infusion pump in which the sliding clamp is attached and locked, viewed from a lateral side and obliquely above the sliding clamp.

When the sliding clamp 20 is pushed into the pump body 30 again, as shown in FIGS. 13 to 15, the clamp slider 54 is pushed by the sliding clamp 20 so as to slide toward the inside of the pump body 30. This causes the engagement projection 54c of the clamp slider 54 to be engaged with the claw 53a of the slider locking member 53, and the state in which the sliding clamp 20 and the clamp slider 54 are pushed is maintained.

When the sliding clamp 20 is pushed into the pump body 30 further, as shown in FIGS. 11 and 12, the pin 54b of the clamp slider 54 pushed by the sliding clamp 20 presses the pressed portion 55b of the link member 55, so that the link member 55 is rotatably moved. This causes the pressing projection 55a of the link member 55 to come in contact with the receiving portion 35a of the engagement-disengagement piece 35. Consequently, the engagement-disengagement piece 35 slides in a direction (rightward in FIG. 11) for disengaging the latches, so that the latches 41 in the door 40 are disengaged from the engagement-disengagement piece 35. Thus, the door 40 is opened by an urging force by an urging member (e.g., a torsion spring), which is not illustrated in the drawings.

After the door 40 is opened, the sliding clamp 20 is pulled out so as to be removed from the clamp attachment portion 31b. Along with this, the infusion tube 10 is also removed from the tube insertion grooves 31a1.

Thus, according to the infusion pump 1 configured as above, it is possible to suppress occurrence of free flow caused by a mistake in procedures for attachment and detachment of the sliding clamp 20 with respect to the infusion tube 10, a mistake in procedures for attachment and detachment of the infusion tube 10 with respect to the pump body 30, unintended opening of the door 40, and/or the like. Therefore, it is possible to secure excellent safety in applying the technique of the present invention particularly to medical infusion devices and the like.

The above-described embodiment is configured such that the infusion tube 10 is penetrated in a horizontal direction. However, in addition to this, the present invention encompasses, as other examples, aspects in which an infusion tube 10 is penetrated in a vertical direction or an oblique direction.

Note that the present invention is not limited to the descriptions of the embodiments above, and may be suitably modified as far as the spirit and the scope of the present invention are not changed.

What is claimed is:

1. An infusion pump comprising:
a pump body including a tube attachment portion to which an infusion tube is to be attached detachably; and
a door pivotably supported by the pump body so that the tube attachment portion is openable and closable by the door, wherein
the pump body includes: a clamp attachment portion into which a sliding clamp is to be inserted and set, the sliding clamp being configured to close or release the infusion tube by moving in a direction intersecting with the infusion tube; and a release operator configured to be operated in the clamp attachment portion in order to transfer the sliding clamp from a close mode to a release mode, and
the release operator is configured to be locked, in response to opening movement of the door, so that the release operator is inoperable for releasing, and is configured to be unlocked in response to closing movement of the door.

2. The infusion pump according to claim 1, further comprising
an engagement-disengagement member configured to move between a lock position and an unlock position, the lock position causing the engagement-disengagement member to be engaged with the release operator for locking the release operator so that the release operator is inoperable for releasing, the unlock position causing the engagement-disengagement member to come apart from the release operator for unlocking the release operator, wherein
the engagement-disengagement member is configured to be in the lock position while the door is opened, and to move to the unlock position as a result of coming in sliding contact with the door that is closing.

3. The infusion pump according to claim 1, wherein the release operator is provided in such a manner that the release operator is allowed to be pushed, and the pump body includes an interlocking mechanism configured to move, in response to movement of the release operator in a direction in which the release operator is pushed, the sliding clamp in a direction for releasing the infusion tube.

4. The infusion pump according to claim 3, wherein the interlocking mechanism includes a holding mechanism configured to hold the infusion tube in response to movement of the release operator in the direction in which the release operator is pushed, and the interlocking mechanism is configured to move the sliding clamp in the direction for the releasing, in a state in which the infusion tube is held by the holding mechanism.

5. The infusion pump according to claim 1, wherein the clamp attachment portion is configured to hold the sliding clamp inserted thereinto, in such a manner that the sliding clamp is allowed to be pushed, and the pump body includes a latch mechanism configured to be locked in response to closing of the door, and to be unlocked in response to pushing of the sliding clamp.

6. The infusion pump according to claim 1, wherein the pump body includes a valve mechanism configured to be opened and closed by respective states of the infusion tube attached to the tube attachment portion, the states including a state in which the infusion tube attached to the tube attachment portion is not pressed from a radially outer side, and a state in which the infusion tube attached to the tube attachment portion is pressed from the radially outer side, and the valve mechanism is configured to be closed in response to closing movement of the door, and to be opened in response to opening movement of the door.

* * * * *